United States Patent [19]

Kan et al.

[11] Patent Number: 4,937,012

[45] Date of Patent: Jun. 26, 1990

[54] LOW TEMPERATURE STABLE POLYMETHYLENE POLYPHENYLENE POLYISOCYANATES

[75] Inventors: Peter T. Kan, Plymouth, Mich.; John W. Lightsey, Baton Rouge, La.

[73] Assignee: BASF Corporation, Parsippany, N.J.

[21] Appl. No.: 85,883

[22] Filed: Aug. 14, 1987

Related U.S. Application Data

[63] Continuation-in-part of Ser. No. 695,206, Jan. 25, 1985, abandoned.

[51] Int. Cl.$^5$ .................... C08G 18/74; C08G 18/75
[52] U.S. Cl. ............................ 252/182.21; 521/161
[58] Field of Search ......................... 252/182, 182.21

[56] References Cited

U.S. PATENT DOCUMENTS

| | | | |
|---|---|---|---|
| 3,449,256 | 6/1969 | Farrissey et al. | 252/182 |
| 3,969,262 | 7/1976 | Wagner | 252/182 |
| 4,031,026 | 6/1977 | Ibbotson | 252/182 |
| 4,229,347 | 10/1980 | Holt et al. | 540/202 |
| 4,234,693 | 11/1980 | Wooler | 521/107 |
| 4,241,131 | 12/1980 | Bailey | 428/262 |
| 4,284,073 | 8/1981 | Narayan et al. | 252/182 |
| 4,424,288 | 1/1984 | Patton et al. | 521/99 |
| 4,438,252 | 3/1984 | Carroll et al. | 252/182 |
| 4,442,280 | 4/1984 | Grögler et al. | 252/182 |
| 4,448,938 | 5/1984 | Braynincky et al. | 525/457 |
| 4,452,923 | 6/1984 | Carroll et al. | 252/182 |

Primary Examiner—John Kight, III
Assistant Examiner—Dennis R. Daley
Attorney, Agent, or Firm—Rupert B. Hurley, Jr.

[57] ABSTRACT

Low temperature stable polymethylene polyphenylene polyisocyanates are composed of crude polymethylene polyphenylene polyisocyanate containing from about 50 to about 80 percent by weight 2-ring diphenylmethane diisocyanate wherein from about 65 to about 93 weight percent of the 2-ring diisocyanate is 4,4'- and from about 7 to about 35 weight percent is 2,4'- and furthermore the composition contains from about 1 to about 5 weight percent carbodiimide-uretonimine structure. The polyisocyanates are useful in preparing polyurethane foams.

3 Claims, No Drawings

LOW TEMPERATURE STABLE POLYMETHYLENE POLYPHENYLENE POLYISOCYANATES

This is a continuation-in-part of application Ser. No. 695,206 filed Jan. 25, 1985 now abandoned.

BACKGROUND OF THE INVENTION

1. Field of the Invention

The present invention concerns low temperature stable organic polyisocyanates. More particularly, the present invention relates to low temperature stable polymethylene polyphenylene polyisocyanates and to polyurethane foams prepared therefrom.

2. Prior Art

U.S. Pat. No. 3,449,256 teaches a process for the preparation of polyisocyanates stable at a temperature of about 15° C. The present invention relates to compositions of polyisocyanates which are stable at temperature of 0° C. for at least two weeks.

U.S. Pat. No. 4,448,938 teaches of an isocyanate composition having low temperature stability wherein the composition is composed of a mixture of a reaction product of diphenylmethane diisocyanate with a polyether of an alcohol or amine of molecular weight 600 to 10,000 and a uretonimine modified diphenylmethane diisocyanate.

SUMMARY OF THE INVENTION

Low temperature stable organic polyisocyanates are prepared by partially reacting a crude polymethylene polyphenylene polyisocyanate containing from about 50 to about 80 weight percent 2-ring diphenylmethane diisocyanate in the presence of an effective amount of a carbodiimidization catalyst. The reaction proceeds to the extent that the polyisocyanate has a uretonimine content from about 1 to 5 weight percent. The polyisocyanate compositions may also be prepared by blending various crude and purified polyisocyanates to give the desired compositions.

DESCRIPTION OF THE PREFERRED EMBODIMENTS

In accordance with the present invention, low temperature stable carbodiimide-uretonimine modified organic polyisocyanates useful for the preparation of polyurethane foam products and the like are prepared by heating a polyisocyanate composition consisting essentially of a crude polymethylene polyphenylene polyisocyanate containing from about 50 to about 80 percent by weight 2-ring diphenylmethane diisocyanate wherein from about 65 to about 93 weight of the 2-ring diisocyanate is 4,4'-, and from about 7 to 35 weight percent is 2,4'- and diphenylmethane diisocyanate in the presence of a catalytically effective amount of a carbodiimidization catalyst. The reaction proceeds to the extent that the 2-ring diphenylmethane diisocyanate has a carbodiimide-uretonimine content from about 1 to about 5 weight percent. The catalyst is generally employed at a concentration ranging from 0.0004 part to 5.0 parts per 100 parts of organic polyisocyanates. Preferably, the catalyst is employed at a concentration ranging from 0.0004 to 1 part per 100 parts of the polyisocyanate. The temperatures employed are those over 30° C. Generally, the range is 50° to 250° C., preferably from about 50° to 120° C. and 200° to 230° C. The time required for carrying out this reaction is dependent upon the quantity of catalyst employed. However, the time can vary from about 0.5 hour to 6 hours. When the catalyst is employed in the preferred amount, the reaction time ranges from 0.5 hour to 4 hours. After the required reaction time period has elapsed the resulting product is cooled to temperatures less than 30° C. Optionally, the reaction product may be treated at the reaction temperature or lower with catalyst deactivators which include salts such as magnesium chloride dihydrate, acid chlorides such as benzoyl chlorides and acetyl chlorides, acids such as hydrochloric acid, oxalic acid, phosphoric acid, benzene-sulfonic acid, toluene-sulfonic acid, methanesulfonic acid or trifluoromethanesulfonic acid, sulfonyl chlorides such as benzene-sulfonyl chloride, toluenesulfonyl chloride and the like. Other deactivators which may be employed are such agents as dimethylsulfate, alkyl o,p-toluenesulfonates, methyl chloride and similar compounds as disclosed in U.S. Pat. No. 3,769,318.

The preferred composition is also prepared by blending a crude polymethylene polyphenylene polyisocyanate with purified 4,4'-diphenylmethane diisocyanate and purified 2,4'-diphenylmethane diisocyanate wherein the blended composition contains from about 50 to about 80 weight percent 2-ring diphenylmethane diisocyanate of which about 65 to 93 weight percent is the 4,4'-isomer and from about 7 to about 35 weight percent is the 2,4'-isomer. The remainder of the composition comprises a polyisocyanate having a functionality greater than 2. The composition also contains from about 1 to about 5 weight percent carbodiimide-uretonimine structure. Preferably the 2,4'-diphenylmethane diisocyanate is from about 7 to about 12 weight percent of the 2-ring diisocyanate and the 2-ring diisocyanate is from about 60 to about 70 weight percent.

In the presence of excess polyisocyanate, the carbodiimide and uretonimine structure exists in equilibrium as shown below.

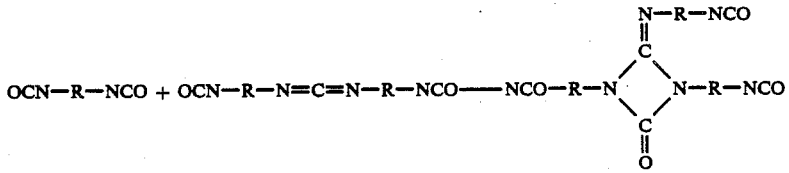

The organic polyisocyanates of the present invention are useful in the preparation of rigid, semi-flexible, or flexible polyurethane foams. The polyurethane foams in accordance herewith are prepared by reacting the organic polyisocyanate and an active hydrogen-containing compound in the presence of urethane catalysts as are well known to those skilled in the art. The foams prepared accordingly display equivalent properties compared to those obtained when employing modified polyisocyanates of the prior art or the polyisocyanates of commerce.

The polyisocyanate compositions of the instant invention may be prepared by employing well-known carbodiimide-promoting compounds as catalysts. The carbodiimide catalysts employed in accordance with the invention can be any of those known in the art as being useful in the conversion of an isocyanate to the corresponding carbodiimide. Illustrative of such catalysts are:

(a) phospholene 1-oxides and 1-sulfides having the formulae:

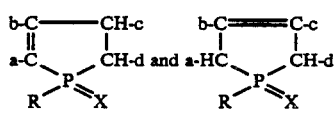

wherein a, b, c and d are each selected from the group consisting of hydrogen and hydrocarbyl from 1 to 12 carbon atoms inclusive, R is selected from the group consisting of lower alkyl and aryl and X is selected from the group consisting of oxygen and sulfur. The above phospholene compounds and methods for their preparation are described in U.S. Pat. Nos. 2,663,737; 2,663,738; and 2,853,473. The 3-phospholenes can be isomerized readily to the corresponding 2-phospholenes by thermal-treatment or by refluxing with an aqueous based as disclosed by Quinn et al, Journal American Chemical Society, 33, 1024, 1968. Representative compounds within the above class are 1-phenyl-2-phospholene-1-oxide; 3-methyl-1-phenyl-3-phospholene-1-oxide; 3-methyl-1-phenyl2-phospholene-1-oxide; 1-phenyl-2-phospholene-1-sulfide; 1-ethyl-2-phospholene-1-oxide; 1-ethyl-3-methyl-2-phospholene-1-oxide; 1-ethyl-3-methyl-2-phospholene-1-sulfide; and the isomeric phospholanes corresponding to the above-named compounds. Also, polymer bound phospholene oxide may be employed specifically those having recurring units, for example,

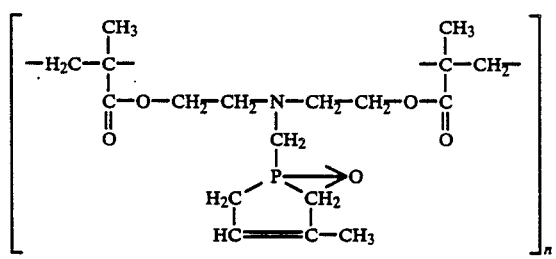

as disclosed in U.S. Pat. No. 4,105,643, and those of the following structure as disclosed in U.S. Pat. No. 4,105,642.

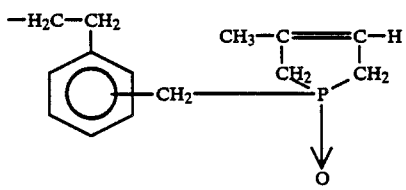

(b) diaza- and oxaza-phospholanes and -phosphorinanes

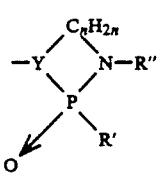

wherein $C_nH_{2n}$ represents alkylene from 1 to 12 carbon atoms, inclusive, at least one and not more than three adjacent carbon atoms and said alkylene radical forming a chain, one end of which is attached to Y, the other end of which is attached to N, thereby completing the heterocyclic ring; R' is selected from the group consisting of hydrocarbyl containing 1 to 12 carbon atoms, inclusive; and halo, nitro, alkoxy, alkyl, mercapto, and cyano-substituted hydrocarbyl from 1 to 12 carbon atoms, inclusive; R" is hydrocarbyl containing from 1 to 12 carbon atoms, inclusive, and Y is selected from the group consisting of —O— and —NR"— wherein R" has the significance as defined above. The above compounds and methods for their preparation are described in U.,S. Pat. No. 3,522,303. Representative examples of such compounds are: 2-ethyl-1,3-dimethyl-1,3,2-diazaphospholane-2-oxide; 2-chloromethyl-1,3-dimethyl-1,3,2-diazaphospholane-2-oxide; 2-trichloromethyl-1,3-dimethyl-1,3,2-diazaphospholane-2-oxide; 2-phenyl-1,3-dimethyl-1,3,2-diazaphospholane2-oxide; 2-phenyl-1,3-dimethyl-1,3,2-diaza-phosphorinane-2-oxide; 2-benzyl-1,3-dimethyl-1,3,2-diazaphospholane-2-oxide; 2-allyl-1,3-dimethyl-1,3,2-diazaphospholane-2-oxide; 2-bromomethyl-1,3-dimethyl-1,3,2-diazaphospholane-2-oxide; 2-cyclohexyl-1,3-dimethyl-1,3,2-diazaphospholane-2-oxide; 2-(2-ethoxyethyl)-1,3-dimethyl-1,3,2-diazaphospholane-2-oxide; and 2-naphthyl-1,3,2-dimethyl-1,3,2-diazaphospholane-2-oxide.

(c) Triaryl arsines wherein the aryl groups are free from substituents containing reactive hydrogen atoms, said arsine being represented by the formula:

wherein each of R, $R_1$ and $R_2$ represents the same or different aryl moieties having from 6 to 12 carbon atoms, inclusive. Such compounds are described in U.S. Pat. No. 3,406,198. Representative examples are: triphenylarsine, tris(p-tolyl)arsine, tris(p-methoxyphenyl)arsine, tris(p-ethoxyphenyl)arsine, tris(p-chlorophenyl)arsine, tris(p-fluorophenyl)arsine, tris(2,5-xylyl)arsine, tris(p-cyanophenyl)arsine, tris(1-naphthyl)arsine, tris(p-methylmercaptophenyl)arsine, tris(p-biphenylyl)arsine, p-chlorophenylbis-(p-tolyl)arsine and phenyl(p-chlorophenyl)(p-bromophenyl)-arsine.

(d) Also included are compounds of the formula:

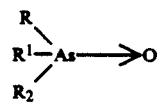

wherein each R, $R_1$ and $R_2$ represents the same or different alkyl or aryl groups having from 6 to 12 carbon atoms, inclusive. Representative examples of such are:

triphenylarsine oxide, triethylarsine oxide, and polymer bound arsine oxide containing recurring units such as are described in U.S. Pat. No. 4,143,063:

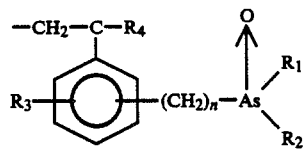

wherein $R_1$ and $R_2$ are hydrocarbyl from 1 to 12 carbon atoms inclusive, $R_3$ is hydrogen, chloro or methyl, $R_4$ is hydrogen or methyl, and n is 0 or 1.

(e) Metallic derivatives of acetylacetone such as the beryllium, aluminum, zirconium, chromium, and iron derivatives thereof as disclosed in U.S. Pat. No. 3,152,131.

(f) Phosphate esters of the formula:

$$(RO)_3PO$$

wherein R is hydrocarbyl from 1 to 12 carbon atoms, inclusive. Such esters and methods for their preparation are disclosed in U.S. Pat. No. 3,056,835. Representative examples are trimethylphosphate, triethylphosphate, ethyldipropylphosphate, triisopropylphosphate, triallylphosphate, triphenylphosphate, and tricresylphosphate.

(g) Phosphine oxides of the formula:

$$R_3PO$$

wherein R is hydrocarbyl from 1 to 12 carbon atoms, inclusive. Representative examples are triethylphosphine oxide, tributylphosphine oxide, triphenylphosphine oxide, and tris(chloromethyl)phosphine oxide.

(h) Metal complexes derived from a d-group transition element and $\pi$-bonding ligand selected from the group consisting of carton monoxide, nitric oxide, hydrocarbylisocyanides, trihydrocarbylphosphine, trihydrocarbylarsine, trihydrocarbylstilbine, and dihydrocarbylsulfide wherein hydrocarbyl in each instance contains from 1 to 12 carbon atoms, inclusive, provided that at least one of the $\pi$-bonding ligands in the complex is carbon monoxide or hydrocarbylisocyanide. Such complexes and methods for the preparation are disclosed in U.S. Pat. No. 3,406,197. Representative examples of such complexes are iron pentacarbonyl, di-iron pentacarbonyl, tungsten hexacarbonyl, molybdenum hexacarbonyl, chromium hexacarbonyl, dimanganese decacarbonyl, nickel tetracarbonyl, ruthenium pentacarbonyl, and the complex of iron tetracarbonyl:methylisocyanide.

The term "hydrocarbyl" from 1 to 12 carbon atoms inclusive employed herein means the monovalent radical obtained by removing one hydrogen atom from a parent hydrocarbon having the stated carbon atom content. Illustrative of such groups are alkyl such as methyl-, ethyl-, propyl-, butyl-, pentyl-, hexyl-, heptyl-, octyl-, nonyl-, decyl-, undecyl-, undodecyl-, including isomeric forms thereof; alkenyl such as allyl, butenyl, pentenyl, hexenyl, heptenyl, octenyl, nonenyl, decenyl, undecenyl, and dodecenyl, including isomeric forms thereof; cycloalkyl such as cyclobutyl, cyclopentyl, cyclohexyl, cycloheptyl, cyclooctyl, and the like; cycloalkenyls such as cyclopentenyl, cyclohexenyl, cycloheptenyl, and the like; aralkyl such as benzyl, phenethyl, phenylpropyl, benzhydryl, naphthylmethyl, and the like; and aryls such as phenyl, tolyl, xylyl, naphthyl, biphenylyl, and the like.

The term "lower alkyl", as used herein, means alkyl from 1 to 6 carbon atoms, inclusive, such a methyl, ethyl, propyl, butyl, pentyl, hexyl and isomeric forms thereof.

The preferred carbodiimide catalysts are the 3-phospholene oxides. The most preferred carbodiimide catalysts are the 1-aryl-3-lower alkyl-3-phospholene 1-oxide and 1,3-di(lower alkyl)-3-phospholene 1-oxide. The most preferred species are 1-phenyl-3-methyl-3-phospholene 1-oxide and 1-ethyl-3-methyl-3-phospholene-1-oxide, and the tris-(chloromethyl)phosphine oxide. Organotin compounds may also be employed in the present invention.

In accordance with the present invention, rigid, semi-flexible, flexible and microcellular foams may be prepared by the reaction of the organic polyisocyanate compositions with polyols in the presence of urethane catalysts, blowing agents, surfactants and other additives which may be deemed necessary.

Flexible foams are generally defined as having a high tensile to compressive strength ratio (25% deflection) from 15 to 60 or 70 to 1, high elongation, a fast recovery rate and a high elastic limit. Rigid foams on the other hand have a high ratio of compressive to tensile strength, 0.5 to 1 or greater low elongation (less than 10%), a low recovery rate from distortion and a low elastic limit. Typical polyols which may be employed in the preparation of the foams of the instant invention include polyhydroxyl-containing polyesters, polyoxyalkylene polyether polyols, polyhydroxy-terminated polyurethane polymers, polyhydroxyl-containing phosphorus compounds, and alkylene oxide adducts of polyhydric sulfur-containing esters, polyacetals, aliphatic polyols or diols, ammonia, and amines including aromatic, aliphatic and heterocyclic amines as well as mixtures thereof. Alkylene oxide adducts of compounds which contain two or more different groups within the abovedefined classes may also be used such as amino alcohols which contain an amino group and a hydroxyl group. Also, alkylene oxide adducts of compounds which contain one —SH group and one —OH group as well as those which contain an amino group and a —SH group may be used. Generally, the equivalent weight of the polyols for rigid foams will vary from about 53 to 700, with functionalities from 3 to 8. The equivalent weight of polyols for flexible foams will range from about 1000 to about 3000 with functionalities from 2 to 4.

Any suitable hydroxy-terminated polyester may be used such as are obtained, for example, from polycarboxylic acids and polyhydric alcohols. Any suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, $\alpha$-hydromuconic acid, $\beta$-hydromuconic acid, $\alpha$-butyl-$\alpha$-ethyl-glutaric acid, $\alpha$, $\beta$-diethylsuccinic acid, isophthalic acid, terphthalic acid, phthalic acid, hemimellitic acid, and 1,4-cyclohexanedicarboxylic acid. Any suitable polyhydric alcohol may be used such as ethylene glycol, propylene glycol, trimethylene glycol, 1,2-butanediol, 1,3-butanediol, 1,4-butanediol, 1,2-pentanediol, 1,4-pentanediol, 1,5-pentanediol, 1,6-hexanediol, 1,7-heptanediol, glycerol, 1,1,1-trimethylolpropane, 1,1,1-trimethylolethane, 1,2,6-hexanetriol, α-methyl glucoside, pentaerythritol, and sorbitol. Also included within the term "polyhydric alcohol" are compounds derived from phenol such as 2,2-bis(4-hydroxyphenyl)-propane, commonly known as Bisphenol A.

Any suitable polyoxyalkylene polyether polyol may be used such as the polymerization product of an alkylene oxide with a polyhydric alcohol. Any suitable polyhydric alcohol may be used such as those disclosed above for use in the preparation of the hydroxy-terminated polyesters. Any suitable alkylene oxide may be used such as ethylene oxide, propylene oxide, butylene oxide, amylene oxide, and mixtures of these oxides. The polyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide. The polyalkylene polyether polyols may have either primary or secondary hydroxyl groups. Included among the polyether polyols are polyoxyethylene glycol, polyoxypropylene glycol, polyoxybutylene glycol, polytetramethylene glycol, block copolymers, for example, combinations of polyoxypropylene and polyoxyethylene glycols, poly-1,2-oxybutylene and polyoxyethylene glycols, poly-1,4-tetramethylene and polyoxyethylene glycols, and copolymer glycols prepared from blends or sequential addition of two or more alkylene oxides. The polyalkylene polyether polyols may be prepared by any known process such as, for example, the process disclosed by Wurtz in 1859 and *Encyclopedia of Chemical Technology*, Vol. 7, pp. 257–262, published by Interscience Publishers, Inc. (1951) or in U.S. Pat. No. 1,922,459. Polyethers which are preferred include the alkylene oxide addition products of trimethylolpropane, glycerine, pentaerythritol, sucrose, sorbitol, propylene glycol, and 2,2-bis(4-hydroxyphenyl)-propane and blends thereof having equivalent weights of from 100 to 5000.

Suitable polyhydric polythioethers which may be condensed with alkylene oxides include the condensation product of thiodiglycol or the reaction product of a dicarboxylic acid such as is disclosed above for the preparation of the hydroxyl-containing polyesters with any other suitable thioether glycol.

The hydroxyl-containing polyester may also be a polyester amide such as is obtained by including some amine or amino alcohol in the reactants for the preparation of the polyesters. Thus, polyester amides may be obtained by condensing an amino alcohol such as ethanolamine with the polycarboxylic acids set forth above or they may be made using the same components that make up the hydroxyl-containing polyester with only a portion of the components being a diamine such as ethylene diamine.

Polyhydroxyl-containing phosphorus compounds which may be used include those compounds disclosed in U.S. Pat. No. 3,639,542. Preferred polyhydroxyl-containing phosphorus compounds are prepared from alkylene oxides and acids of phosphorus having a $P_2O_5$ equivalency of from about 72 percent to about 95 percent.

Suitable polyacetals which may be condensed with alkylene oxides include the reaction product of formaldehyde or other suitable aldehyde with a dihydric alcohol or an alkylene oxide such as those disclosed above.

Suitable aliphatic thiols which may be condensed with alkylene oxides include alkanethiols containing at least two -SH groups such as 1,2-ethanedithiol, 1,2-propanedithiol, 1,2-propanedithiol, and 1,6-hexanedithiol; alkene thiols such as 2-butene-1,4-dithiol; and alkyne thiols such as 3-hexyne-1,6-dithiol.

Suitable amines which may be condensed with alkylene oxides include aromatic amines such as aniline, o-chloro-aniline, p-aminoaniline, 1,5-diaminonaphthalene, methylene dianiline, the various condensation products of aniline and formaldehyde, and the isomeric diaminotoluenes; aliphatic amines such as methylamine, triisopropanolamine, ethylenediamine, 1,3-diaminopropane, 1,3-diaminobutane, and 1,4-diaminobutane.

The polyurethane foams of the present invention may also be prepared by the reaction of a graft copolymer polyol with the polyisocyanate of the instant invention in the presence of a blowing agent and optionally in the presence of additional polyhydroxyl-containing components, chain-extending agents, catalysts, surface-active agents, stabilizers, dyes, fillers and pigments. Suitable processes for the preparation of cellular polyurethane products are disclosed in U.S. Reissue Pat. No. 24,514 together with suitable machinery to be used in conjunction therewith. For the preparation of microcellular foams, blowing agents are generally not necessary. If desired for more expanded foams, they may be employed. When water is added as the blowing agent, corresponding quantities of excess isocyanate to react with the water and produce carbon dioxide may be used.

It is possible to proceed with the preparation of the polyurethane products by a prepolymer technique wherein an excess of organic polyisocyanate of the instant invention is reacted in a first step with a polyol to prepare a prepolymer having free isocyanate groups which is then reacted in a second step with a polyol or an amine and a blowing agent such as water or a fluorocarbon to prepare a foam. Alternately, the components may be reacted in a single working step commonly known as the "one-shot" technique of preparing polyisocyanurate-polyurethanes products. Furthermore, instead of water, low boiling hydrocarbons such as pentane, hexane, heptane, pentene, and heptene; azo compounds such as azohexahydrobenzodinitrile; halogenated hydrocarbons such as dichlorodifluoromethane, trichlorofluoromethane, dichlorodifluoroethane, vinylidene chloride, and methylene chloride may be used as blowing agents.

Chain-extending agents which may be employed in the preparation of the polyurethane foams include those compounds having at least two functional groups bearing active hydrogen atoms such as water, hydrazine, primary and secondary diamines, amino alcohols, amino acids, hydroxy acids, glycols, or mixtures thereof. A preferred group of chain-extending agents includes water, ethylene glycol, 1,4-butanediol, and primary and secondary diamines which react more readily with the polyisocyanates of the instant invention than does water. These include phenylenediamine, ethylenediamine, diethylenetriamine, N-(2-hydroxypropyl)-ethylenediamine, N,N'-di(2-hydroxypropyl)ethylenediamine, piperazine, and 2-methyl-piperazine.

Any suitable polyurethane promoting catalyst may be used including tertiary amines such as, for example, triethylenediamine, N-methylmorpholine, N-ethylmorpholine, diethylaminoethanol, N-laurylmorpholine, 1-methyl-4(dimethylaminoethyl) piperazine, 3-methoxy-N,N'-dimethylpropylamine, N,N,N'-trimethyl-isopropylproylenediamine, N,N,N',N"-tetraethylpropylenediamine, dimethylbenzylamine, dimethylcycloheylamiine and the like. Other suitable catalysts are, for example, tin compounds such as stannous chloride, tin salts of carboxylic acids, such as dibutyltin di-2-ethyl hexanoate and stannous octoate, as well as other organo metallic compounds such as are disclosed in U.S. Pat. No. 2,846,408. The preferred catalysts for the preparation of polyurethane foams are triethylenediamine, N-methylmorpholine and N-ethylmorpholine and dibutyltin dilaurate.

If desired, a surface-active agent may be employed. Numerous surface-active agents have been found satisfactory. Nonionic surface-active agents are preferred. Of these, the nonionic surface-active agents prepared by the sequential addition of propylene oxide and then ethylene oxide to propylene glycol and the solid or liquid organosilicones have been found particularly desirable. Other surface-active agents which are operative, although not preferred, include polyethylene glycol ethers of long chain alcohols, tertiary amine or alkylolamine salts of long chain alkyl acid sulfate esters, alkylsulfonic esters, and alkylarylsulfonic acids.

The following examples illustrate the nature of the invention. All parts are by weight unless otherwise stated. The following abbreviations are used herein:

Polyol A is a propylene oxide, ethylene oxide adduct of trimethylolpropane containing 13 weight percent ethylene oxide and having a hydroxyl number of 35.

Polyol B is a mixture of 23 weight percent of polyol A and 77 weight percent of polyol A which was reacted with alpha-glycidyl ether to give about 0.3 mole of unsaturation per mole of polyol and further reacted with 31 weight percent of a 1:1 mixture of acrylonitrile:styrene and having a hydroxyl number of 24.

Polyol C is an ethylene oxide adduct of ethylenediamine having a hydroxyl number of 760.

Polyol D is a propylene oxide, ethylene oxide adduct of toluenediamine containing 30 weight percent ethylene oxide and having a hydroxyl number of 390.

Polyol E is a propylene oxide adduct of toluenediamine having a hydroxyl number of 450.

Polyol F is a diethylene glycol diester of phthalic anhydride having a hydroxyl number of 260.

DEG is diethylene glycol.

Dabco R-8020 is a catalyst sold by M&T Corporation.

Dabco 33LV is a catalyst sold by M&T Corporation.

Freon 11-A is trichloromonofluoromethane sold by duPont Corporation.

Niax A-1 is a catalyst sold by Union Carbide Corporation.

EXAMPLES 1-9

The isocyanates of Examples 1-9 were prepared by blending crude polymethylene polyphenylene polyisocyanate with purified 4,4'-diphenylmethane diisocyanate and purified 2,4'-diphenylmethane diisocyanate to produce the compositions of Table I. The compositions were stored at 0° C. for at least two weeks with daily visual observations. The products deemed stable were those which did not display more than a trace of haziness for a two week period. The results are tabulated in Table I. The 2-ring content was essentially composed of 2,4'- and 4,4'-diphenylmethane diisocyanate.

TABLE I

| Example | Isocyanate | % 2-ring | % 2,4'- in 2-ring | % Uretonimine | Stable at 0° C. for two weeks |
|---|---|---|---|---|---|
| 1 | A | 61.8 | 11.9 | 3 | yes |
| 2 | B | 61.8 | 8.3 | 2.6 | yes |
| 3 | C | 65.6 | 8.1 | 4.7 | yes |
| 4 | D | 61.8 | 4.4 | 2.6 | no |
| 5 | E | 61.8 | 6.4 | 2.6 | no |
| 6 | F* | 65 | 6 | — | no |
| 7 | G | 65 | 15 | — | no |
| 8 | H | 65 | 2 | — | no |
| 9 | I | 55 | 32 | — | yes |

*Commercial polymeric polymethylene polyphenylene polyisocyanate.

EXAMPLES 10 and 11

All of the components, except for the isocyanate as listed in Table II, were blended together at a temperature of about 77° F. Approximately 225 parts of this blend were poured into a suitable container followed immediately by the required quantity of Isocyanate A and I to give an index of 100. This blend was mixed rapidly for about 5 seconds and was poured into an automotive crash pad mold which was heated to 100° F. The mold was sealed and the mixture was allowed to cure for 4 minutes at 150° F. The semi-flexible foam was then removed and the physical properties as listed were determined employing well-known standard ASTM methods. The results indicate the Isocyanate I, while exhibiting non-freezing properties, does result in CLD and compression set properties which are deemed not acceptable for automotive crash pad use.

TABLE II

| Example | 10 | 11 |
|---|---|---|
| Formulation, pbw | | |
| Polyol A | 95 | 95 |
| Polyol B | 20 | 20 |
| Polyol C | 3 | 3 |
| H₂O | 1.5 | 2.5 |
| Triethanolamine | 1 | 1 |
| Dimethylethanolamine | 0.396 | 0.396 |
| Dabco 33LV | 0.462 | 0.462 |
| Niax A-1 | 0.09 | 0.09 |
| Isocyanate A (Index) | 100 | — |
| Isocyanate I (Index) | — | 100 |
| Physical Properties | | |
| Density, pcf | 5.73 | 5.48 |
| CLD, 25% psi | 4.7 | 6.9* |
| Elongation, % | 85 | 83 |
| Tensile, psi | 22 | 28 |
| Compression Set, 50% | 17.9 | 31.3* |

*Unacceptable

EXAMPLES 12 and 13

All of the components except for the isocyanate, as listed in Table III, were blended together and charged into a tank at 55° F. The isocyanates were charged into a tank at 77° F. The two liquids were mixed by high pressure impingement mixing and poured into panel molds. The panels were allowed to cure for 15 minutes before demolding. The foam panels were then checked for their physical properties employing well-known standard ASTM test methods. The resulting rigid foams have comparable physical properties.

TABLE III

| Example | 12 | 13 |
|---|---|---|
| Formulation, pbw | | |
| Polyol D | 60 | 60 |

TABLE III-continued

| Example | 12 | 13 |
| --- | --- | --- |
| Polyol E | 15 | 15 |
| Polyol F | 23 | 23 |
| Diethylene glycol | 2 | 2 |
| L-5340 | 1 | 1 |
| Dabco R-8020 | 0.9 | 0.9 |
| Dabco 33LV | 0.3 | 0.3 |
| H₂O | 1.2 | 1.2 |
| Freon 11A | 47 | 47 |
| Isocyanate A (Index) | 110 | — |
| Isocyanate F (Index) | — | 110 |
| Physical Properties | | |
| Density, pcf | | |
| core (packed panel) | 1.45 | 1.44 |
| overall (packed panel) | 1.75 | 1.74 |
| Compressive strength | | |
| yield point | 20.2 | 21.8 |
| 10% deflection | 18.5 | 18.7 |
| yield point | 14.2 | 12.3 |
| 10% deflection | 13.4 | 12.2 |
| MVT | 1.34 | 1.29 |
| Friability, wt. loss | 2.58 | 3.46 |
| % closed cells | 86.7/97.3 | 86.2/97.2 |
| K factor | | |
| 0 days @ RT | 0.112 | 0.111 |
| 10 days @ 140° F. | 0.131 | 0.128 |
| 30 days @ 140° F. | 0.144 | 0.140 |
| 100 days @ 140° F. | 0.157 | 0.154 |
| Water absorption, % | 2.7 | 1.8 |
| Dimensional stability (% volume) | | |
| @ 100° F. + 100% R.H. | | |
| 1 day | 1.0 | 1.0 |
| 2 days | 0.7 | 0.6 |
| 7 days | 2.1 | 1.9 |
| 28 days | 3.1 | 3.5 |
| @ 158° F. | | |
| 1 day | 1.3 | 1.0 |
| 2 days | 1.7 | 1.1 |
| 7 days | 3.8 | 3.1 |
| 28 days | 6.5 | 6.9 |
| @ −20° F. | | |
| 1 day | −3.4 | −1.1 |
| 2 days | −4.0 | 0.3 |
| 7 days | −5.7 | −8.3 |
| 28 days | −7.6 | −12.8 |

The embodiments of the invention in which an exclusive privilege or property is claimed are defined as follows:

1. A polyisocyanate composition which is storage stable at temperatures of about 0° C. which composition consisting essentially of a crude polymethylene polyphenylene polyisocyanate containing from about 50 to 80 weight percent 2-ring diphenylmethane diisocyanate, wherein from about 7 to about 35 weight percent of the 2-ring diisocyanate is 2,4′-diphenylmethane diisocyanate, from about 65 to about 93 weight percent of the 2-ring diisocyanate is 4,4′-diphenylmethane diisocyanate and wherein the 2-ring diisocyanate contains from 1 to 5 weight percent uretonimine structure the remainder of said polyisocyanate composition comprising a polyisocyanate having a functionality greater than 2.

2. The polyisocyanate composition of claim 1 wherein the 2,4′-diphenylmethane diisocyanate is from about 7 to about 12 weight percent of the 2-ring diisocyanate.

3. The polyisocyanate composition of claim 1 wherein the 2-ring diisocyanate is from about 60 to about 70 weight percent.

* * * * *